(12) United States Patent
Stein

(10) Patent No.: US 6,770,753 B2
(45) Date of Patent: Aug. 3, 2004

(54) PHOSPHOROTHIOATE ANTISENSE HEPARANASE OLIGONUCLEOTIDES

(75) Inventor: Cy Stein, New City, NY (US)

(73) Assignee: The Trustees of Columbia University in the City of New York, New York, NY (US)

( * ) Notice: Subject to any disclaimer, the term of this patent is extended or adjusted under 35 U.S.C. 154(b) by 0 days.

(21) Appl. No.: 09/899,440

(22) Filed: Jul. 5, 2001

(65) Prior Publication Data

US 2003/0092158 A1 May 15, 2003

(51) Int. Cl.$^7$ .............................................. C07H 21/04
(52) U.S. Cl. ........................... 536/24.5; 514/44; 435/6; 435/325; 435/375; 536/23.1
(58) Field of Search .............................. 536/24.5, 23.1, 536/24.3, 24.32; 435/6, 325, 375; 514/44

(56) References Cited

U.S. PATENT DOCUMENTS

| | | | | |
|---|---|---|---|---|
| 5,484,908 A | * | 1/1996 | Froehler et al. | ......... 536/24.31 |
| 5,801,154 A | * | 9/1998 | Baracchini et al. | ........... 514/44 |

FOREIGN PATENT DOCUMENTS

| | | | | |
|---|---|---|---|---|
| WO | WO 96/08559 | * | 3/1996 | ............ C12N/9/24 |
| WO | WO 00/52178 | * | 9/2000 | ........... C12N/15/56 |

OTHER PUBLICATIONS

Taylor et al., Drug Discov Today. Dec. 1999; 4(12):562–567.*

Braasch, D. A. Biochemistry. Apr. 2002; 41(14): 4503–4510.*

Branch, A. D., (1998). Trends Biochem Sci. Feb. 1998; 23(2):45–50.*

Agrawal, S. Trends Biotechnol. Oct. 1996; 14(10):376–87.*

Gewirtz et al., Proc. Natl. Acad. Sci. v93, pp. 3161–3163.*

Tamm, I. et al. The Lancet. Aug. 2001, 358: 489–497.*

Dempsey, Laurie A. et al. Heparanase Expression In Invasive Trophoblasts and Acute Vascular Damage. Glycobiology 2000; 10:467–475.

Kussie, P.H. et al. (1999) Biochem. *Biophys. Res. Comm.* 261:183–187 (Exhibit 2).

Vlodasky, I. et al, (1999) *Nature Medicine* 5:793–802 (Exhibit 3).

* cited by examiner

*Primary Examiner*—Sean McGarry
*Assistant Examiner*—James Douglas Schultz
(74) *Attorney, Agent, or Firm*—John P. White; Cooper & Dunham LLP

(57) ABSTRACT

The present invention provides antisense phosphorothioate oligonucleotides that specifically inhibit the translation of heparanase. The invention also provides various methods of reducing angiogenesis and metastasis of tumors in a subject using said antisense phosphorothioate oligonucleotides. Finally the invention provides pharmaceutical compositions comprising the said antisense phosphorothioate oligonucleotides as active ingredients.

11 Claims, 3 Drawing Sheets

```
atgctgctgc gctcgaagcc tgcgctgccg ccgccgctgc tgatgctgct gctcctgggg
ccgctgggtc ccctctccc  tggcgccctg ccccgacctg cgcaagcaca gcaggacgtc
gtggacctgg acttcttcac ccaggagccg ctgcacctgg tgagcccctc gttcctgtcc
gtcaccattg acgccaacct ggccacggac ccgcggttcc tcatcctcct gggttctcca
aagcttcgta ccttggccag aggcttgtct cctgcgtacc tgaggtttgg tggcaccaag
acagacttcc taattttcga tcccaagaag gaatcaacct tgaagagag  aagttactgg
caatctcaag tcaaccagga tatttgcaaa tatggatcca tccctcctga tgtggaggag
aagttacggt tggaatggcc ctaccaggag caattgctac tccgagaaca ctaccagaaa
aagttcaaga acagcaccta ctcaagaagc tctgtagatg tgctatacac ttttgcaaac
tgctcaggac tggacttgat ctttggccta aatgcgttat taagaacagc agatttgcag
tggaacagtt ctaatgctca gttgctcctg gactactgct cttccaaggg gtataacatt
tcttgggaac taggcaatga acctaacagt ttccttaaga aggctgatat tttcatcaat
gggtcgcagt taggagaaga ttttattcaa ttgcataaac ttctaagaaa gtccaccttc
aaaaatgcaa aactctatgg tcctgatgtt ggtcagcctc gaagaaagac ggctaagatg
ctgaagagct tcctgaaggc tggtggagaa gtgattgatt cagttacatg gcatcactac
tatttgaatg gacggactgc taccagggaa gatttctaa  accctgatgt attggacatt
tttatttcat ctgtgcaaaa agtttttccag gtggttgaga gcaccaggcc tggcaagaag
gtctggttag gagaaacaag ctctgcatat ggaggcggag cgccttgct  atccgacacc
tttgcagctg gctttatgtg gctggataaa ttgggcctgt cagcccgaat gggaatagaa
gtggtgatga ggcaagtatt ctttggagca ggaaactacc atttagtgga tgaaaacttc
gatcctttac ctgattattg gctatctctt ctgttcaaga aattggtggg caccaaggtg
ttaatggcaa gcgtgcaagg ttcaaagaga aggaagcttc gagtatacct tcattgcaca
aacactgaca atccaaggta taagaagga  gatttaactc tgtatgccat aaacctccat
aacgtcacca agtacttgcg gttaccctat ccttttttcta acaagcaagt ggataaatac
cttctaagac ctttgggacc tcatggatta ctttccaaat ctgtccaact caatggtcta
actctaaaga tggtggatga tcaaaccttg ccacctttaa tggaaaaacc tctccggcca
ggaagttcac tgggcttgcc agctttctca tatagttttt ttgtgataag aaatgccaaa
gttgctgctt gcatctgaaa ataaaatata ctagtcctga cactgaaaa
```

Figure 3

PHOSPHOROTHIOATE ANTISENSE HEPARANASE OLIGONUCLEOTIDES

BACKGROUND OF THE INVENTION

Heparanase

Cancer is the second leading cause of death in the United States. When cancer has metastasized, it can only be cured by systemic therapy, usually cytotoxic chemotherapy. Alternative methods to prevent tumor spread that would avoid cytotoxic chemotherapy are very desirable.

One area of promise in alternative methods of therapy involves the study of heparanase. Heparanase breaks down heparan—a component of the cell surface and extracellular matrix. It has recently been shown that inhibition of heparanase reduces tumor spread (Kussie, et al. 1999 and Vlodasky, 1999), reducing both tumor neogenesis and angiogenesis.

Antisense Phosphorothioate Oligonucleotides

One way to achieve therapeutically useful targeted inhibition of protein expression is likely going to be through the use of antisense oligonucleotides. Antisense oligonucleotides are small fragments of DNA complementary to a defined sequence on a specified mRNA. The antisense oligonucleotide specifically binds to targets on the mRNA molecule and in doing so inhibits the translation of a specific mRNA into protein.

Antisense oligonucleotide molecules synthesized with a phosphorothioate backbone have proven particularly resistant to exonuclease damage compared to standard deoxyribonucleic acids, and so they are used in preference.

The present study discloses that instead of inhibiting heparanase itself, another method to reduce tumor spread may be to inhibit heparanase protein expression using antisense phosphorothioate oligonucleotides.

SUMMARY OF INVENTION

This invention provides an oligonucleotide having a sequence complementary to a sequence of a ribonucleic acid encoding a heparanase, wherein:

(a) the oligonucleotide hybridizes with the ribonucleic acid under conditions of high stringency and is between 10 and 40 nucleotides in length;

(b) the internucleoside linkages of the oligonucleotide comprise at least one phosphorothioate linkage; and (c) hybridization of the oligonucleotide to the ribonucleic acid inhibits expression of the heparanase, wherein inhibition of heparanase expression means at least a 50% reduction in the quantity of heparanase as follows: (a) a T24 bladder carcinoma cell is exposed to a complex of the oligonucleotide and lipofectin at an oligonucleotide concentration of 1 μM and a lipofectin concentration of 10 μg/ml for 5 hours at 37° C., (b) the complex is completely removed after such exposure, (c) 19 hours later the cell is scraped, washed and extracted in lysis buffer, (d) the nucleus of the cell is removed by centrifugation, (e) the cytoplasmic proteins in the resulting supernatant are separated according to mass by sodium dodecyl sulphate polyacrylamide gel electrophoresis, (f) the protein is transferred to a polyvinylidene difluoride membrane that is incubated at room temperature for 1–2 hours in incubation solution (g) the membrane is exposed to 1 μg/ml of an antibody directed against heparanase at 4° C. for 12 hours, (h) the membrane is exposed to wash buffer and incubated for 1 hour at room temperature in blocking buffer comprising a 1:3,000 dilution of a peroxidase-conjugated secondary antibody directed against an epitope on the antibody directed against heparanase, (i) the membrane is exposed to a chemiluminescent cyclic diacylthydrazide and the oxidation of the cyclic diacylthydrazide by the peroxidase is detected as a chemiluminescent signal, and (j) the signal is quantitated by laser-scanning densitometry as a measure of the amount of heparanase expressed calculated as a percentage of heparanase expression in an untreated cell.

This invention further provides the instant oligonucleotide, wherein the oligonucleotide comprises deoxyribonucleotides.

This invention further provides the instant oligonucleotide, wherein the oligonucleotide comprises ribonucleotides.

This invention further provides the instant oligonucleotide, wherein every internucleoside linkage is a phosphorothioate linkage.

This invention further provides the instant oligonucleotide, wherein the oligonucleotide is between 15 and 25 nucleotides in length.

This invention further provides the instant oligonucleotide, wherein the oligonucleotide is about 20 nucleotides in length.

This invention further provides the instant oligonucleotide, wherein the sequence of the oligonucleotide is selected from the following:

(a) CCCCAGGAGCAGCAGCAGCA (SEQ ID NO: 3);

(b) GTCCAGGAGCAACTGAGCAT (SEQ ID NO: 4); and (c) AGGTGGACTTTCTTAGAAGT (SEQ ID NO: 5).

This invention further provides the instant oligonucleotide, wherein the oligonucleotide further comprises a modified internucleoside linkage.

This invention further provides the instant oligonucleotide, wherein the modified internucleoside linkage is a peptide-nucleic acid linkage, a morpholino linkage, a phosphodiester linkage or a stereo-regular phosphorothioate.

This invention further provides the instant oligonucleotide, wherein the oligonucleotide further comprises a modified sugar moiety.

This invention further provides the instant oligonucleotide, wherein the modified sugar moiety is 2'-O-alkyl oligoribonucleotide.

This invention further provides the instant oligonucleotide, wherein the oligonucleotide further comprises a modified nucleobase.

This invention further provides the instant oligonucleotide, wherein the modified nucleobase is a 5-methyl pyrimidine or a 5-propynyl pyrimidine.

This invention further provides the instant oligonucleotide, wherein the heparanase is a human heparanase.

This invention also provides a method of inhibiting expression of a heparanase in a cell comprising contacting the cell with the instant oligonucleotide under conditions such that the oligonucleotide hybridizes with mRNA encoding the heparanase so as to thereby inhibit the expression of the heparanase.

This invention further provides the instant method, wherein the cell is a cancer cell.

This invention also provides a composition comprising the instant oligonucleotide in an amount effective to inhibit expression of a heparanase in a cell and a carrier.

This invention further provides the instant composition, wherein the oligonucleotide and the carrier are capable of passing through a cell membrane.

This invention further provides the instant composition, wherein the carrier comprises a membrane-permeable cationic reagent.

This invention further provides the instant composition, wherein the cationic reagent is lipofectin.

This invention also provides a method of treating a tumor in a subject which comprises administering to the subject an amount of the instant oligonucleotide effective to inhibit expression of a heparanase in the subject and thereby treat the tumor.

This invention further provides the instant method, wherein the subject is a human being.

This invention further provides the instant method, wherein the treatment of the tumor is effected by reducing tumor growth.

This invention further provides the instant method, wherein the treatment of the tumor is effected by reducing tumor metastasis.

This invention further provides the instant method, wherein the treatment of the tumor is effected by reducing angiogenes is.

This invention also provides a method of treating a subject which comprises administering to the subject an amount of the instant oligonucleotide effective to inhibit expression of a heparanase in the subject and thereby treat the subject.

This invention further provides the instant method, wherein the subject is a human being.

This invention also provides the use of the instant oligonucleotide for the preparation of a pharmaceutical composition for treating a tumor in a subject which comprises admixing the oligonucleotide in an amount effective to inhibit expression of a heparanase in the subject, with a pharmaceutical carrier.

This invention also provides an oligonucleotide having a sequence complementary to a sequence of a ribonucleic acid encoding a heparanase, wherein:

(a) the oligonucleotide hybridizes with the ribonucleic acid under conditions of high stringency and is between 10 and 40 nucleotides in length;

(b) the internucleoside linkages of the oligonucleotide comprise at least one phosphorothioate linkage; and (c) hybridization of the oligonucleotide to the ribonucleic acid inhibits expression of the heparanase.

Figure 1:
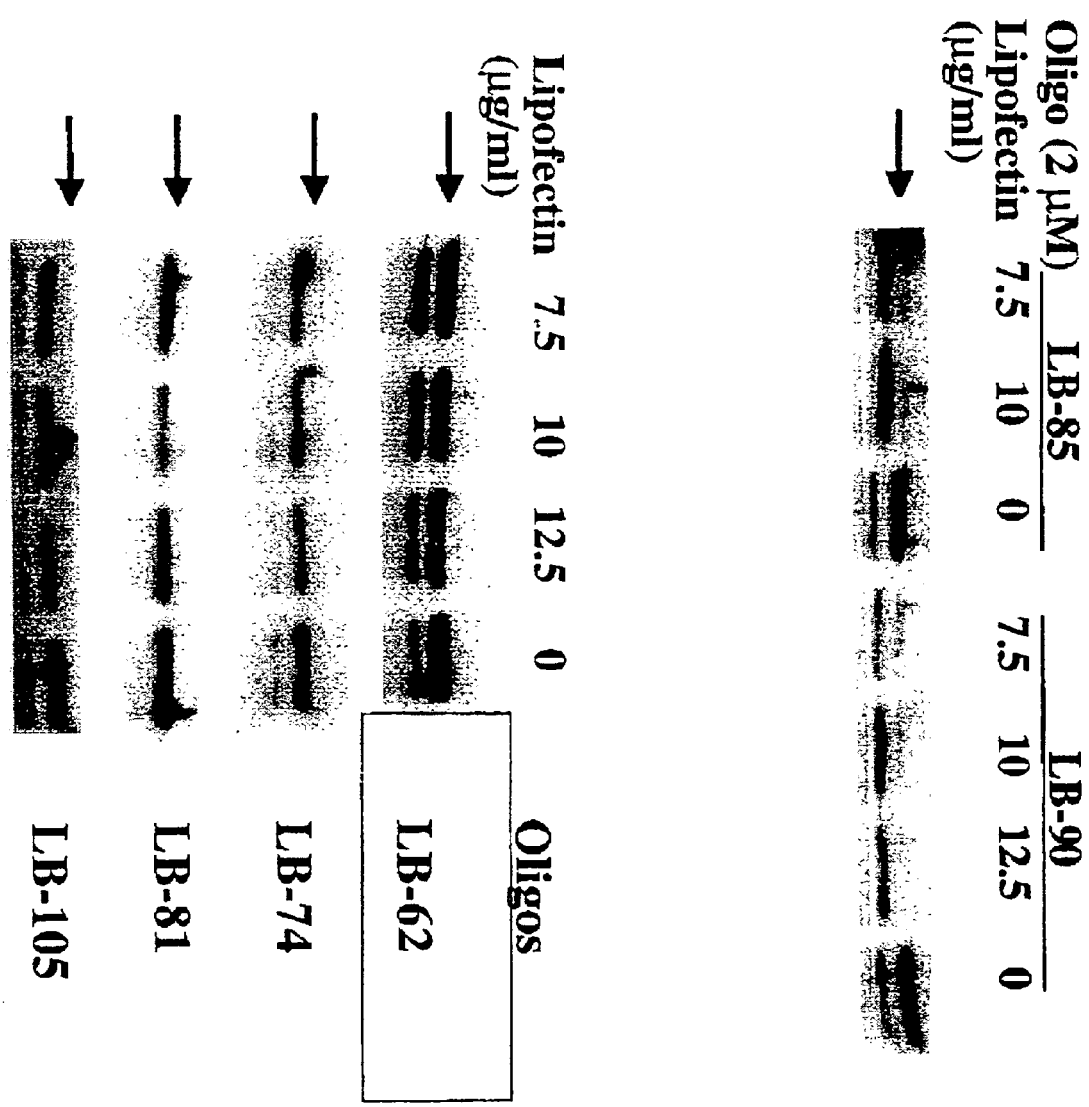
FIG. 1

Western Blot showing reduction of heparanase protein expression by LB85 (90% compared to untreated control) and LB90 (95% compared to control). Also shown are other phosphorothioate oligonucleotides that were tested but had no significant effect on heparanase protein expression.

FIG. 2

Northern blot showing downregulation of heparanase protein expression by LB85, LB90 and LB65. Also shown are other phosphorothioate oligonucleotides that were ineffective at downregulating mRNA expression as well as the G3DPH control.

FIG. 3

This figure shows the DNA sequence encoding Human heparanase protein.

DETAILED DESCRIPTION OF THE INVENTION

The following definitions are presented as an aid in understanding this invention:

| | |
|---|---|
| CDNA | Complementary DNA; |
| DNA | Deoxyribonucleic Acid; |
| DTT | (-)-1,4-Dithio-L-Threitol; |
| ER | Endoplasmic Reticulum; |
| G3PDH | Glycerol-3-Phosphate Dehydrogenase. |
| Hepes | N-(2-Hydroxyethyl)piperazine-N'-(2-ethane-sulfonic acid) |
| HIV | Human Immunodeficiency Virus; |
| ICAM- 1 | Intercellular Adhesion Molecule-1; |
| Ig | Immunoglobulin; |
| MEM | Modified Eagle's Medium |
| mRNA | Messenger RNA; |
| PBS | Phosphate Buffered Saline; |
| RNA | Ribonucleic Acid; |
| SDS | Sodium Dodecyl Sulphate; |
| SSC | Saline-Sodium Citrate Buffer; |
| UV | Ultra Violet. |

"Administer" shall mean any of the various methods and delivery systems known to those skilled in the art. The administering can be performed, for example, orally, via implant, transmucosally, transdermally and subcutaneously.

"Carrier" shall mean any of the various carriers known to those skilled in the art. "Pharmaceutical carrier" shall mean the same, excepting that the carrier shall be pharmaceutically acceptable. In one embodiment, the carrier is a membrane-permeable cationic reagent, preferably lipofectin. In another embodiment, the carrier is a non-covalently linked peptide complex. In another embodiment the carrier is a covalent linked peptide complex, comprising, for example, a pH sensitive fusogenic peptide. In other embodiments the carriers are polyamidodendrimers; transferrin polylysine; polyglycolic acid co-polymers and any delivery in polymers that can be used to nanoencapsulate, such as polylactic acid. In another embodiment the oligonucleotide is modifed by addition of a 5' cholesteryl; and in other embodiments by 5' lipid or alkyl.

The following carriers are set forth, in relation to their most commonly associated delivery systems, by way of example, and do not preclude combinations of carriers.

Dermal delivery systems include, for example, aqueous and nonaqueous gels, creams, multiple emulsions, microemulsions, liposomes, ointments, aqueous and non-aqueous solutions, lotions, aerosols, hydrocarbon bases and powders, and can contain excipients such as solubilizers, permeation enhancers (e.g., fatty acids, fatty acid esters, fatty alcohols and amino acids), and hydrophilic polymers (e.g., polycarbophil and polyvinylpyrolidone). In one embodiment, the pharmaceutically acceptable carrier is a liposome or a transdermal enhancer. Examples of liposomes which can be used in this invention include the following: (1) CellFectin, 1:1.5 (M/M) liposome formulation of the cationic lipid N,NI,NII,NIII-tetramethyl-N,NI,NII,NIII-tetrapalmityl-spermine and dioleoyl phosphatidylethanolamine (DOPE) (GIBCO BRL); (2) Cytofectin GSV, 2:1 (M/M) liposome formulation of a cationic lipid and DOPE (Glen Research); (3) DOTAP (N-[1-(2,3-dioleoyloxy)-N,N, N-tri-methyl-ammoniummethylsulfate) (Boehringer Mannheim); and (4) Lipofectamine, 3:1 (M/M) liposome formulation of the polycationic lipid DOSPA and the neutral lipid DOPE (GIBCO BRL).

Transmucosal delivery systems include patches, tablets, suppositories, pessaries, gels and creams, and can contain excipients such as solubilizers and enhancers (e.g., propylene glycol, bile salts and amino acids), and other vehicles (e.g., polyethylene glycol, fatty acid esters and derivatives, and hydrophilic polymers such as hydroxypropylmethylcellulose and hyaluronic acid).

Injectable drug delivery systems include solutions, suspensions, gels, microspheres and polymeric injectables, and can comprise excipients such as solubility-altering agents (e.g., ethanol, propylene glycol and sucrose) and polymers (e.g., polycaprolactones and PLGA's). Implantable systems include rods and discs, and can contain excipients such as PLGA and polycaprolactone.

Oral delivery systems include tablets and capsules. These can contain excipients such as binders (e.g., hydroxypropylmethylcellulose, polyvinyl pyrrolidone, other cellulosic materials and starch), diluents (e.g., lactose and other sugars, starch, dicalcium phosphate and cellulosic materials), disintegrating agents (e.g., starch polymers and cellulosic materials) and lubricating agents (e.g., stearates and talc).

"Blocking buffer" shall mean 5% non-fat milk in phosphate buffered saline containing 0.5% Tween-20, wherein Tween-20 is polyoxyethylene (20) sorbitan monolaurate.

"Centrifugation" shall mean centrifugation at 8,000 cpm for 10 min. at 4° C.

"Chemiluminescent cyclic diacylthydrazide" shall mean Luminol (Amersham).

"Complex" shall mean, when applied to a "complex" of oligonucleotide and lipofectin, a solution comprising Lipofectin diluted in 100 μl of Opti-MEM medium (Gibco BRL) to give a final concentration of 10 μg/ml, and phosphorothioate oligonucleotides diluted in 100 μl of Opti-MEM to give a final concentration of 1 μM mixed gently and preincubated at room temperature for 30 min to allow complexes to form and then diluted with 800 μl of Opti-MEM media.

"Extracted in lysis buffer" shall mean exposing cells to 40–50 mL of 10 mM Hepes, pH 7.9, 10 mM KCl, 1.5 mM $MgCl_{-}$, 15 μg/ml aprotinin, leupeptin, 50 μg/ml Pefablock SC, 0.5 mM DTT, and 0.3% of Nonidet P40 at 4° C. for 10 min.

"Heparanase" shall mean the protein encoded by the nucleotide sequence shown in FIG. 3 (SEQ ID NO: 17) and having the amino acid sequence SEQ ID NO: 18, and any variants thereof, whether artificial or naturally occurring.

"Incubation solution" shall mean Blotto A (Amersham) [5% bovine serum albumin in phosphate buffered saline containing 0.5% Tween-20, wherein Tween-20 is polyoxyethylene(20)sorbitan monolaurate.]

"Inhibit" shall mean to slow, stop or otherwise impede.

"Modified nucleobase" shall mean, when applied to an oligonucleotide, nucleotide bases that are substituted or modified. Apart from the bases of adenine, guanine, cytosine, and thymine, other natural bases such as inosine, deoxyinosine, and hypoxanthine are acceptable in the oligonucleotide moiety useful in the subject invention. In addition, isosteric purine 2'deoxy-furanoside analogues, 2'-deoxynebularine or 2'deoxyxanthosine, or other purine and pyrimidine analogues such as 5-methyl pyrimidine or a 5-propynyl pyrimidine may also be used.

"Modified sugar" shall mean, when applied to an oligonucleotide moiety, a sugar modified or replaced so as to be ribose, glucose, sucrose, or galactose, or any other sugar. Alternatively, the oligonucleotide may have one or more of its sugars substituted or modified in its 2' position, i.e. 2'alkyl or 2'-O-alkyl. An example of a 2'-O-allyl sugar is a 2'-O-methylribonucleotide. Further, the oligonucleotide may have one or more of its sugars substituted or modified to form an α-anomeric sugar. "oligonucleotide" shall mean an oligonucleotide or oligodeoxyribonucleotide or an oligoribonucleotide.

"Phosphorothioate", when applied to an oligonucleotide, shall mean an oligonucleotide in which a sulfur atom replaces one or more of the non-bridging oxygen atoms in one or more phosphodiester linkages, i.e. an oligonucleotlde having one or more phosphorothiodiester linkages. Each phosphorothiodiester linkage can occur as either an Rp or Sp diastereomer. A bridging oxygen atom is an oxygen atom in a phosphodiester linkage of a nucleic acid which joins phosphorous to a sugar.

One or more of the phosphorothiodiester linkages of the oligonucleotide moiety may be modified by replacing one or both of the two bridging oxygen atoms of the linkage with analogues such as —NH, —$CH_2$, or —S. Other oxygen analogues known in the art may also be used.

A phosphorothioate oligonucleotide may be stereo regular, stereo non-regular or stereo random. A stereo regular phosphorothioate oligonucleotide is a oligonucleotide in which all the phosphodiester linkages or phosphorothiodiester linkages polarize light in the same direction. Each phosphorous in each linkage may be either an Sp or Rp diastereomer. Phosphorothioate oligonucleotides which are created in an automated synthesizer are stereo random which means that each phosphorous atom in the phosphorothioate oligonucleotide has a 50% chance of being either an Sp or an Rp diastereomer.

"Specifically hybridize", when referring to the action of the instant oligonucleotide on a target mRNA molecule, shall mean the annealing of the instant oligonucleotide to the target mRNA molecule, based on sequence complementarity, without annealing to another mRNA molecule lacking a sequence complementary to the instant oligonucleotide. The propensity for hybridization between nucleic acids depends on the temperature and ionic strength of their milieu, the length of the oligonucleotide and the degree of complementarity. The effect of these parameters on hybridization is well known in the art (see Sambrook, 1989).

"Stringent conditions" or "Stringency", shall refer to the conditions for hybridization as defined by the nucleic acid, salt, and temperature. These conditions are well known in the art and may be altered. Numerous equivalent conditions comprising either low or high stringency depend on factors such as the length and nature of the sequence (DNA, RNA, base composition), nature of the target (DNA, RNA, base composition), milieu (in solution or immobilized on a solid substrate), concentration of salts and other components (e.g., formamide, dextran sulfate and/or polyethylene glycol), and temperature of the reactions (within a range from about 5° C. below the melting temperature of the probe to about 20° C. to 25° C. below the melting temperature). One or more factors be may be varied to generate conditions of either low or high stringency different from, but equivalent to, the above listed conditions. As will be understood by those of skill in the art, the stringency of hybridization may be altered in order to identify or detect identical or related polynucleotide sequences.

"Subject" shall mean any animal, such as a human, a primate, a mouse, a rat, a guinea pig or a rabbit.

"Variants" shall mean proteins having at least 80%, preferably at least 90%, more preferably at least 95% similarity with SEQ ID NO: 18. As used herein "similar" is used to denote which sequences when aligned have similar (identical or conservatively substituted) amino acids in like positions or regions, where identical or conservatively replaced amino acids are those which do not alter the activity or function of the protein as compared to the starting protein.

"Wash buffer" shall mean phosphate buffered saline with 0.5% Tween-20, wherein Tween-20 is polyoxyethylene(20) sorbitan monolaurate.

"Washed" shall mean washed in phosphate buffered saline.

Having due regard to the preceding definitions, the present invention provides an oligonucleotide having a sequence complementary to a sequence of a ribonucleic acid encoding a heparanase, wherein:

(a) the oligonucleotide hybridizes with the ribonucleic acid under conditions of high stringency and is between 10 and 40 nucleotides in length;

(b) the internucleoside linkages of the oligonucleotide comprise at least one phosphorothioate linkage; and (c) hybridization of the oligonucleotide to the ribonucleic acid inhibits expression of the heparanase, wherein inhibition of heparanase expression means at least a 50% reduction in the quantity of heparanase as follows: (a) a T24 bladder carcinoma cell is exposed to a complex of the oligonucleotide and lipofectin at an oligonucleotide concentration of 1 $\mu$M and a lipofectin concentration of 10 $\mu$g/ml for 5 hours at 37° C., (b) the complex is completely removed after such exposure, (c) 19 hours later the cell is scraped, washed and extracted in lysis buffer, (d) the nucleus of the cell is removed by centrifugation, (e) the cytoplasmic proteins in the resulting supernatant are separated according to mass by sodium dodecyl sulphate polyacrylamide gel electrophoresis, (f) the protein is transferred to a polyvinylidene difluoride membrane that is incubated at room temperature for 1–2 hours in incubation solution (g) the membrane is exposed to 1 $\mu$g/ml of an antibody directed against heparanase at 4° C. for 12 hours, (h) the membrane is exposed to wash buffer and incubated for 1 hour at room temperature in blocking buffer comprising a 1:3,000 dilution of a peroxidase-conjugated secondary antibody directed against an epitope on the antibody directed against heparanase, (i) the membrane is exposed to a chemiluminescent cyclic diacylthydrazide and the oxidation of the cyclic diacylthydrazide by the peroxidase is detected as a chemiluminescent signal, and (j) the signal is quantitated by laser-scanning densitometry as a measure of the amount of heparanase expressed calculated as a percentage of heparanase expression in an untreated cell.

In one embodiment every internucleoside linkage is a phosphorothioate linkage. In one embodiment the ribonucleic acid molecule is a messenger ribonucleic acid molecule. In a further embodiment the ribonucleic acid molecule encodes for heparanase protein. In one embodiment the hybridization of the oligonucleotide to the ribonucleic acid molecule inhibits heparanase protein expression. In one embodiment the heparanase protein is human. In one embodiment the oligonucleotide comprises deoxyribonucleotides. In another embodiment the oligonucleotide comprises ribonucleotides. In one embodiment the oligonucleotide sequence is a minimum of 10 and a maximum of 40 nucleobases in length. In another embodiment the oligonucleotide sequence is a minimum of 15 and a maximum of 25 nucleobases in length. In the preferred embodiment the phosphorothioate oligonucleotide is about 20 nucleobases in length.

This invention further provides the instant oligonucleotide, wherein the sequence is selected from the following group:

(a) CCCCAGGAGCAGCAGCAGCA (SEQ ID NO: 3);

(b) GTCCAGGAGCAACTGAGCAT (SEQ ID NO: 4); and (c) AGGTGGACTTTCTTAGAAGY (SEQ ID NO: 5).

In one embodiment hybridization occurs at target residues 137–156 of the instant heparanase mRNA molecule (see SEQ ID NO: 17) for SEQ ID NO: 3, residues 707–726 for SEQ ID NO: 4 and residues 852–871 for SEQ ID NO: 5.

This invention further provides the instant oligonucleotide, wherein the oligonucleotide further comprises a modified internucleoside linkage. In different embodiments the modified internucleoside linkage is a peptide-nucleic acid linkage, a morpholino linkage, a phosphodiester linkage or a stereo-regular phosphorothioate.

This invention further provides the instant oligonucleotide, wherein the oligonucleotide further comprises a modified sugar moiety. In one embodiment the modified sugar moiety is 2'-O-alkyl oligoribonucleotide.

This invention further provides the instant oligonucleotide sequence, wherein the sequence further comprises a modified nucleobase. In one embodiment the modified nucleobase is a 5-methyl pyrimidine. In one embodiment the modified nucleobase is a 5-propynyl pyrimidine.

This invention also provides a method of inhibiting expression of a heparanase in a cell comprising contacting the cell with the instant oligonucleotide under conditions such that the oligonucleotide hybridizes with mRNA encoding the heparanase so as to thereby inhibit the expression of the heparanase. In one embodiment the cell is a mammalian cell. In a further embodiment the cell is a human cell. In the preferred embodiment the cell is a cancer cell.

This invention also provides a composition comprising the instant oligonucleotide in an amount effective to inhibit expression of a heparanase in a cell and a carrier. In one embodiment the instant composition is capable of passing through a cell membrane. In one embodiment the instant composition comprises a membrane-permeable cationic reagent. In one embodiment the instant reagent is lipofectin. In one embodiment the cell is a mammalian cell. In a further embodiment the cell is a cancer cell. In a further embodiment the cell is a human cell.

This invention also provides method of treating a tumor in a subject which comprises administering to the subject an amount of the instant oligonucleotide effective to inhibit expression of a heparanase in the subject and thereby treat the tumor. In the preferred embodiment the subject is human. In one embodiment the tumor is treated by effecting a reduction in tumor growth. In one embodiment the tumor is treated by effecting a reduction in tumor metastasis. In one embodiment the tumor is treated by effecting a reduction in angiogenesis.

This invention also provides a method of treating a subject which comprises administering to the subject an amount of the instant oligonucleotide effective to inhibit expression of a heparanase in the subject and thereby treat the subject.

In one embodiment the subject has an abnormality that is treated by inhibiting heparanase expression. In one embodiment the subject has an abnormality that is treated by inhibiting angiogenesis. In the preferred embodiment the subject is human.

This invention also provides the use of the instant oligonucleotide for the preparation of a pharmaceutical composition for treating a tumor in a subject which comprises admixing the oligonucleotide in an amount effective to inhibit expression of a heparanase in the subject, with a pharmaceutical carrier. In the preferred embodiment the subject is human.

This invention also provides an oligonucleotide having a sequence complementary to a sequence of a ribonucleic acid encoding a heparanase, wherein:

(a) the oligonucleotide hybridizes with the ribonucleic acid under conditions of high stringency and is between 10 and 40 nucleotides in length;
(b) the internucleoside linkages of the oligonucleotide comprise at least one phosphorothioate linkage; and
(c) hybridization of the oligonucleotide to the ribonucleic acid inhibits expression of the heparanase. In one embodiment inhibition of heparanase expression means at least a 50% reduction in the quantity of heparanase in particular as follows: (a) a T24 bladder carcinoma cell is exposed to a complex of the oligonucleotide and lipofectin at an oligonucleotide concentration of about 1 $\mu$M and a lipofectin concentration of about 10 $\mu$g/ml for about 5 hours at 37° C., (b) the complex is completely removed after such exposure, (c) about 19 hours later the cell is scraped, washed and extracted in lysis buffer, (d) the nucleus of the cell is removed by centrifugation, (e) the cytoplasmic proteins in the resulting supernatant are separated according to mass by sodium dodecyl sulphate polyacrylamide gel electrophoresis, (f) the protein is transferred to a polyvinylidene difluoride membrane that is incubated at room temperature for about 1–2 hours in incubation solution (g) the membrane is exposed to about 1 ug/ml of an antibody directed against heparanase at 4° C. for about 12 hours, (h) the membrane is exposed to wash buffer and incubated for about 1 hour at room temperature in blocking buffer comprising a 1:3,000 dilution of a peroxidase-conjugated secondary antibody directed against an epitope on the antibody directed against heparanase, (i) the membrane is exposed to a chemiluminescent cyclic diacylthydrazide and the oxidation of the cyclic diacylthydrazide by the peroxidase is detected as a chemiluminescent signal, and (j) the signal is quantitated by laser-scanning densitometry as a measure of the amount of heparanase expressed calculated as a percentage of heparanase expression in an untreated cell.

The following Experimental Details are set forth to aid in an understanding of the invention, and are not intended, and should not be construed, to limit in any way the invention set forth in the claims which follow thereafter.

EXPERIMENTAL DETAILS

Antisense phosphorothioate oligonucleotides inhibit heparanase protein expression: Inhibition of heparanase protein expression by anti-heparanase phosphorothioate oligonucleotides was demonstrated by Western blotting, as is shown in FIG. 1. T24 bladder carcinoma cells were treated with the phosphorothioate oligonucleotides complexed with Lipofectin. The optimum concentration of the oligomer was 1 $\mu$M. The optimum concentrations of Lipofectin were 10 and 12.5 $\mu$g/ml. The optimum incubation time of the cells with complexes was 5 h, and expression of heparanase protein was assayed after a further 19 h of incubation in complete media in the absence of complex. The most active sequences were LB 85 (SEQ ID NO: 4), 90 (SEQ ID NO: 5) and 65 (SEQ ID NO: 3). The expression of heparanase protein for LB85, 90 and 65 was reduced by approximately 90, 95 and 75%, respectively (FIG. 1). No other oligomers produced any significant reduction in target protein levels.

Figure 2:
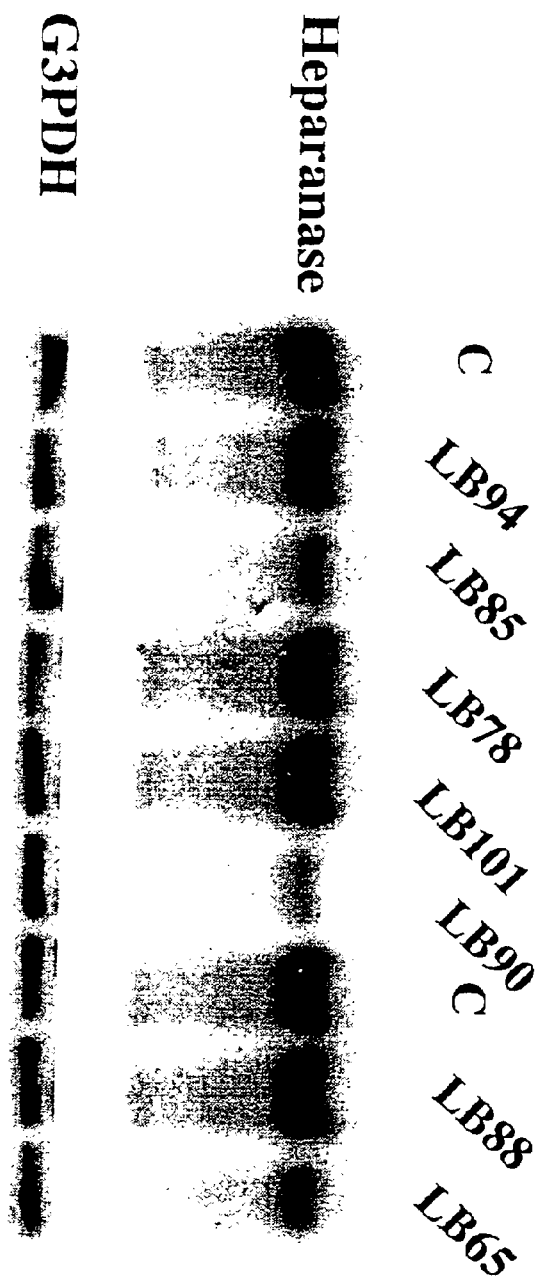

Downregulation of Heparanase protein mRNA by antisense heparanase phosphorothioate oligonucleotides: Heparanase protein mRNA expression in T24 cells treated with anti-heparanase phosphorothioate oligonucleotides was evaluated by Northern blotting, using the heparanase cDNA fragment as a probe. The 4.4 and 2.0 kB Heparanase protein mRNA species were easily visualized (FIG. 2). Significantly, only the phosphorothioate oligonucleotides that demonstrated activity in the Western blot were active in the Northern blot. None of the four control phosphorothioate oligonucleotides (LB78—SEQ ID NO: 7, LB88—SEQ ID NO: 8, LB94—SEQ ID NO: 6, LB101—SEQ ID NO: 9), which were entirely inactive in the Western blot, demonstrated any activity vs. the untreated controls in the Northern blot. The extent of downregulation for LB90 (SEQ ID NO: 5) was approximately 90%, and for LB65 (SEQ ID NO: 3) and LB85 (SEQ ID NO: 4) approximately 75% (FIG. 2). These results confirm the Western analysis, and demonstrate that these phosphorothioate oligonucleotides cause a sequence specific anti-heparanase effect.

The Heparanase protein mRNA blots were then stripped and reprobed with a control glycerol-3-phosphate dehydrogenase cDNA probe (G3PDH). The data demonstrated essentially equal RNA loading in each lane, and no decrease in levels of this mRNA species.

MATERIALS AND METHODS

Cells: T24 cells were grown at 37° C. in a humidified 5% $CO_2$ incubator in McCoy's 5A medium (Gibco BRL, Grand Island, N.Y.), containing 10% (v/v) heat inactivated (56° C.) fetal bovine serum (FBS) (Gibco BRL, Grand Island, N.Y.), supplemented with 25 mM Hepes, 100 units/mL penicillin G sodium and 100 g/mL streptomycin sulfate.

Reagents: Anti-human heparanase mouse monoclonal antibody HP-130 (IgGl subclass) were obtained from Insight (Rehovot, Israel). Anti-mouse horseradish peroxidase conjugated secondary antibody was from Amersham, Arlington Heights, Ill. Lipofectin was purchased from Gibco BRL.

Synthesis of phosphorothioate oligonucleotides: The all-phosphorothioate oligonucleotides used in these studies were synthesized on an Applied Biosystems (Foster City, Calif.) model 380B DNA synthesizer by standard methods. Sulfurization was performed using tetraethyithiuram disulfide/acetonitrile. Following cleavage from controlled pore glass support, oligodeoxynucleotides were base deblocked in ammonium hydroxide at 60° C. for 8 h and purified by reversed-phase HPLC [0.1M triethylammonium bicarbonate/acetonitrile; PRP-1 support]. Oligomers were detritylated in 3% acetic acid and precipitated with 2% lithiumperchlorate/acetone, dissolved in sterile water and reprecipitated as the sodium salt from 1 M NaCl/ethanol. Concentrations of the full length species were determined by UV spectroscopy.

The sequences of the phosphorothioate oligonucleotides used were (5' to 3'):

| | | |
|---|---|---|
| TGGGCTCACCTGGCTGCTCC | (LB63) | SEQ ID NO:1; |
| CGCCAGCTGCCGCGCAGCGG | (LB62) | SEQ ID NO:2; |
| CCCCAGGAGCAGCAGCAGCA | (LB65) | SEQ ID NO:3; |
| GTCCAGGAGCAACTGAGCAT | (LB85) | SEQ ID NO:4; |
| AGGTGGACTTTCTTAGAAGT | (LB90) | SEQ ID NO:5; |
| TCAAATAGTAGTGATGCCAT | (LB94) | SEQ ID NO:6; |
| CTTCTCCTCCACATCAGGAG | (LB78) | SEQ ID NO:7; |
| ATTGATGAAAATATCAGCCT | (LB88) | SEQ ID NO:8; |
| TTATCCAGCCACATAAAGCC | (LB101) | SEQ ID NO:9; |
| AGCGCAGGCTTCGAGCGCAG | (LB64) | SEQ ID NO:10; |
| GATAGCCAATAATCAGGTAA | (LB105) | SEQ ID NO:11; |
| GGTGCCACCAAACCTCAGGT | (LB74) | SEQ ID NO:12; |
| GAGCCCCAGCGCCCTTTTCT | (LB60) | SEQ ID NO:13; |
| GGAGAACCCAGGAGGATGAG | (LB72) | SEQ ID NO:14; |
| CTACAGAGCTTCTTGAGTAG | (LB81) | SEQ ID NO:15; and |
| TATACCTTGGATTGTCAGTG | (LB109) | SEQ ID NO:16. |

Treatment of cells with phosphorothicate oligonucleotide/Lipofectin complexes: Cells were seeded the day before the experiment in 6-well plates at a density of $25–30 \times 10^4$ cells per well to be 65–70% confluent on the day of the experiment. The transfections were performed in Opti-MEM medium (Gibco BRL) as per the manufacturer's instructions. Lipofectin was diluted in 100 μl of Opti-MEM medium to give a final concentration of 10 or 12.5 μg/ml, and phosphorothioate oligonucleotides were diluted in 100 μl of Opti-MEM to give a final concentration of 1 μM. The solutions were mixed gently and preincubated at room temperature for 30 min to allow complexes to form. Then, 800 μl of Opti-MEM media was added, the solution mixed, and overlaid on the cells that were pre-washed with Opti-MEM. The cells were then incubated at 37° C. for 5 h, re-fed with fresh complete media containing 10% FBS (no phosphorothioate oligonucleotide/Lipofectin complexes present), and allowed to incubate for an additional 19 h before cell lysis and extract preparation.

Western Blot Analysis: Cells treated with phosphorothioate cligonucleotide-lipid complexes were scraped, washed with cold PBS and then extracted in 40–50 mL of 10 mM Hepes, pH 7.9, 10 mM KCl, 1.5 mM $MgCl_2$, 15 μg/ml aprotinin, leupeptin, 50 μg/ml Pefablock SC, 0.5 mM DTT, and 0.3% of Nonidet-P40 at 4° C. for 10 min. The nuclei were removed by centrifugation for 10 min at 4° C., and cytoplasmic protein concentrations in the supernatants were determined using the Bio-Rad protein assay system (Bio-Rad Laboratories, Richmond, Calif.). Aliquots of cytoplasmic extracts, containing 35–40 μg of protein, were resolved by 10% PAGE. Proteins were then transferred to PVDF membranes (Amersham, Arlington Heights, Ill.), and the filters incubated at room temperature for 1–2 h in Blotto A [5% BSA in PBS containing 0.5% Tween 20]. The filters were then probed with 1 μg/ml of the anti-heparanase antibody in Blotto A at 4° C. overnight. After washing in PBS-0.5% Tween 20 buffer (3×7 min, room temperature), the filters were incubated for 1 h at room temperature in 5% non-fat milk in PBS containing 0.5% Tween-20 with a 1:3,000 dilution of a peroxidase-conjugated secondary antibody (Amersham). After washing (3×10 min), ECL was performed according to the manufacturer's instructions. Protein expression was quantitatively analyzed via laser-scanning densitometry using NIH Image Version 1.61 software. All results were calculated as a percentage of protein expression in treated vs. untreated cells.

Northern Blot Analysis: Total cellular RNA was isolated using TRIZOL Reagent (Gibco BRL). 20–30 μg was resolved on a 1.2% agarose gel containing 1.1% formaldehyde and transferred to Hybond-N nylon membranes (Amersham). A human heparanase cDNA probe (kindly provided by Insight, Rehovot, Israel) was $^{32}$P-radiolabeled with [$-^{32}$P]dCTP by random primer labeling using a commercially available kit (Promega) according to the manufacturer's instructions. The blots were then hybridized with the cDNA probe in 50% formamide, 5×SSC, 5×Denhard's solution, 0.5% SDS, 1% dextran sulfate, and 0.1 mg/ml of salmon sperm DNA overnight at 42° C. The filters were washed at room temperature, twice for 15 min in 2×SSC and 0.1% SDS, once for 20 min in 1×SSC and 0.1% SDS, and finally twice for 15 min in 0.1×SSC and 0.1% SDS at 65° C.

The filters were exposed to Kodak X-ray film for 12–48 h with intensifying screens at −70° C., and then developed. A similar procedure was repeated for the G3PDH control.

REFERENCES

1. Kussie, P. H. et al. (1999) *Biochem. Biophys. Res. Comm.* 261:183–187.
2. Lebedeva et al, (2000) *Eur J Pharm Biopharm. July* 2000; 50(1):101–19.
3. Sambrook et al., "Molecular Cloning: A Laboratory Manual", Second Edition (1989), Cold Spring Harbor Laboratory Press, Cold Spring Harbor, N.Y.
4. Vlodasky, I. et al, (1999) *Nature Medicine* 5:793–802.

What is claimed is:

1. An oligonucleotide which hybridizes with a ribonucleic acid encoding a heparanase having a sequence as set forth in SEQ ID NO:18 and inhibits expression thereof, wherein the sequence of the oligonucleotide is selected from the following:
   (a) CCCCAGGAGCAGCAGCAGCA (SEQ ID NO: 3);
   (b) GTCCAGGAGCAACTGAGCAT (SEQ ID NO:4); or
   (c) AGGTGGACTTTCTTAGAAGT (SEQ ID NO:5).

2. The oligonucleotide of claim 1, wherein the oligonucleotide further comprises a modified internucleoside linkage.

3. The oligonucleotide of claim wherein the modified internucleoside linkage as a peptide-nucleic acid linkage or a morpholino linkage.

4. The oligonucleotide of claim 1, wherein the oligonucleotide further comprises a modified sugar moiety.

5. The oligonucleotide of claim 4, wherein the modified sugar moiety is 2'-O-alkyl oligoribonucleotide.

6. The oligonucleotide of claim 1, wherein the oligonucleotide further comprises a modified nucleobase.

7. The oligonucleotide of claim 4, wherein the modified nucleobase is a 5-methyl pyrimidine or a 5-propynyl pyrimidine.

8. A composition comprising the oligonucleotide of claim 1 in an amount effective to inhibit expression of a heparanase in a cell and a carrier.

9. The composition of claim 8, wherein the oligonucleotide and the carrier are capable of passing through a cell membrane.

10. The composition of claim 9, wherein the carrier comprises a membrane-permeable cationic reagent.

11. The composition of claim 10, wherein the cationic reagent is a 1:1 (w/w) liposome formulation of a cationic lipid N-[1-(2,3-dioleyloxy)propyl]-N,N,N-trimethylammonium chloride and dioleoyl phosphatidylethanolamine.

* * * * *

```
                            SEQUENCE LISTING

<160> NUMBER OF SEQ ID NOS: 18

<210> SEQ ID NO 1
<211> LENGTH: 20
<212> TYPE: DNA
<213> ORGANISM: Artificial Sequence
<220> FEATURE:
<221> NAME/KEY: misc_feature
<222> LOCATION: ()..()
<223> OTHER INFORMATION: anitsense oligonucleotide  LB63

<400> SEQUENCE: 1
tgggctcacc tggctgctcc                                                 20

<210> SEQ ID NO 2
<211> LENGTH: 20
<212> TYPE: DNA
<213> ORGANISM: Artificial Sequence
<220> FEATURE:
<221> NAME/KEY: misc_feature
<222> LOCATION: ()..()
<223> OTHER INFORMATION: antisense oligonucleotide LB62

<400> SEQUENCE: 2
cgccagctgc cgcgcagcgg                                                 20

<210> SEQ ID NO 3
<211> LENGTH: 20
<212> TYPE: DNA
<213> ORGANISM: Artificial Sequence
<220> FEATURE:
<221> NAME/KEY: misc_feature
<222> LOCATION: ()..()
<223> OTHER INFORMATION: antisense oligonucleotide LB65

<400> SEQUENCE: 3
ccccaggagc agcagcagca                                                 20

<210> SEQ ID NO 4
<211> LENGTH: 20
<212> TYPE: DNA
<213> ORGANISM: Artificial Sequence
<220> FEATURE:
<221> NAME/KEY: misc_feature
<222> LOCATION: ()..()
<223> OTHER INFORMATION: antisense oligonucleotide LB85

<400> SEQUENCE: 4
gtccaggagc aactgagcat                                                 20

<210> SEQ ID NO 5
<211> LENGTH: 20
<212> TYPE: DNA
<213> ORGANISM: Artificial Sequence
<220> FEATURE:
<221> NAME/KEY: misc_feature
<222> LOCATION: ()..()
```

<223> OTHER INFORMATION: antisense oligonucleotide LB90

<400> SEQUENCE: 5
aggtggactt tcttagaagt                                          20

<210> SEQ ID NO 6
<211> LENGTH: 20
<212> TYPE: DNA
<213> ORGANISM: Artificial Sequence
<220> FEATURE:
<221> NAME/KEY: misc_feature
<222> LOCATION: ()..()
<223> OTHER INFORMATION: antisense oligonucleotide LB94

<400> SEQUENCE: 6
tcaaatagta gtgatgccat                                          20

<210> SEQ ID NO 7
<211> LENGTH: 20
<212> TYPE: DNA
<213> ORGANISM: Artificial Sequence
<220> FEATURE:
<221> NAME/KEY: misc_feature
<222> LOCATION: ()..()
<223> OTHER INFORMATION: antisense oligonucleotide LB78

<400> SEQUENCE: 7
cttctcctcc acatcaggag                                          20

<210> SEQ ID NO 8
<211> LENGTH: 20
<212> TYPE: DNA
<213> ORGANISM: Artificial Sequence
<220> FEATURE:
<221> NAME/KEY: misc_feature
<222> LOCATION: ()..()
<223> OTHER INFORMATION: antisense oligonucleotide LB88

<400> SEQUENCE: 8
attgatgaaa atatcagcct                                          20

<210> SEQ ID NO 9
<211> LENGTH: 20
<212> TYPE: DNA
<213> ORGANISM: Artificial Sequence
<220> FEATURE:
<221> NAME/KEY: misc_feature
<222> LOCATION: ()..()
<223> OTHER INFORMATION: antisense oligonucleotide LB101

<400> SEQUENCE: 9
ttatccagcc acataaagcc                                          20

<210> SEQ ID NO 10
<211> LENGTH: 20
<212> TYPE: DNA
<213> ORGANISM: Artificial Sequence
<220> FEATURE:
<221> NAME/KEY: misc_feature
<222> LOCATION: ()..()
<223> OTHER INFORMATION: antisense oligonucleotide LB64

<400> SEQUENCE: 10
agcgcaggct tcgagcgcag                                          20

<210> SEQ ID NO 11
<211> LENGTH: 20

<212> TYPE: DNA
<213> ORGANISM: Artificial Sequence
<220> FEATURE:
<221> NAME/KEY: misc_feature
<222> LOCATION: ()..()
<223> OTHER INFORMATION: antisense oligonucleotide LB105

<400> SEQUENCE: 11
gatagccaat aatcaggtaa                                         20

<210> SEQ ID NO 12
<211> LENGTH: 20
<212> TYPE: DNA
<213> ORGANISM: Artificial Sequence
<220> FEATURE:
<221> NAME/KEY: misc_feature
<222> LOCATION: ()..()
<223> OTHER INFORMATION: antisense oligonucleotide LB74

<400> SEQUENCE: 12
ggtgccacca aacctcaggt                                         20

<210> SEQ ID NO 13
<211> LENGTH: 20
<212> TYPE: DNA
<213> ORGANISM: Artificial Sequence
<220> FEATURE:
<221> NAME/KEY: misc_feature
<222> LOCATION: ()..()
<223> OTHER INFORMATION: antisense oligonucleotide LB60

<400> SEQUENCE: 13
gagccccagc gcccttttct                                         20

<210> SEQ ID NO 14
<211> LENGTH: 20
<212> TYPE: DNA
<213> ORGANISM: Artificial Sequence
<220> FEATURE:
<221> NAME/KEY: misc_feature
<222> LOCATION: ()..()
<223> OTHER INFORMATION: antisense oligonucleotide LB72

<400> SEQUENCE: 14
ggagaaccca ggaggatgag                                         20

<210> SEQ ID NO 15
<211> LENGTH: 20
<212> TYPE: DNA
<213> ORGANISM: Artificial Sequence
<220> FEATURE:
<221> NAME/KEY: misc_feature
<222> LOCATION: ()..()
<223> OTHER INFORMATION: antisense oligonucleotide LB81

<400> SEQUENCE: 15
ctacagagct tcttgagtag                                         20

<210> SEQ ID NO 16
<211> LENGTH: 20
<212> TYPE: DNA
<213> ORGANISM: Artificial Sequence
<220> FEATURE:
<221> NAME/KEY: misc_feature
<222> LOCATION: ()..()
<223> OTHER INFORMATION: antisense aligonucleotide LB109

<400> SEQUENCE: 16

|  |  |
|---|---:|
| tataccttgg attgtcagtg | 20 |

<210> SEQ ID NO 17
<211> LENGTH: 1669
<212> TYPE: DNA
<213> ORGANISM: Homo Sapiens

<400> SEQUENCE: 17

|  |  |
|---|---:|
| atgctgctgc gctcgaagcc tgcgctgccg ccgccgctgc tgatgctgct gctcctgggg | 60 |
| ccgctgggtc ccctctcccc tggcgccctg ccccgacctg cgcaagcaca gcaggacgtc | 120 |
| gtggacctgg acttcttcac ccaggagccg ctgcacctgg tgagccctc gttcctgtcc | 180 |
| gtcaccattg acgccaacct ggccacggac ccgcggttcc tcatcctcct gggttctcca | 240 |
| aagcttcgta ccttggccag aggcttgtct cctgcgtacc tgaggtttgg tggcaccaag | 300 |
| acagacttcc taattttcga tcccaagaag gaatcaacct ttgaagagag aagttactgg | 360 |
| caatctcaag tcaaccagga tatttgcaaa tatggatcca ccctcctga tgtggaggag | 420 |
| aagttacggt tggaatggcc ctaccaggag caattgctac tccgagaaca ctaccagaaa | 480 |
| aagttcaaga cagcaccta ctcaagaagc tctgtagatg tgctatacac ttttgcaaac | 540 |
| tgctcaggac tggacttgat ctttggccta aatgcgttat taagaacagc agatttgcag | 600 |
| tggaacagtt ctaatgctca gttgctcctg gactactgct cttccaaggg gtataacatt | 660 |
| tcttgggaac taggcaatga acctaacagt ttccttaaga aggctgatat tttcatcaat | 720 |
| gggtcgcagt taggagaaga ttttattcaa ttgcataaac ttctaagaaa gtccaccttc | 780 |
| aaaaatgcaa aactctatgg tcctgatgtt ggtcagcctc aagaaagac ggctaagatg | 840 |
| ctgaagagct tcctgaaggc tggtggagaa gtgattgatt cagttacatg gcatcactac | 900 |
| tatttgaatg gacggactgc taccagggaa gattttctaa accctgatgt attggacatt | 960 |
| tttatttcat ctgtgcaaaa agttttccag gtggttgaga gcaccaggcc tgcaagaag | 1020 |
| gtctggttag agaaacaag ctctgcatat ggaggcggag cgcccttgct atccgacacc | 1080 |
| tttgcagctg gctttatgtg gctggataaa ttgggcctgt cagcccgaat gggaatagaa | 1140 |
| gtggtgatga ggcaagtatt ctttggagca ggaaactacc atttagtgga tgaaaacttc | 1200 |
| gatcctttac ctgattattg ctatctctct ctgttcaaga aattggtggg caccaaggtg | 1260 |
| ttaatggcaa gcgtgcaagg ttcaaagaga aggaagcttc gagtatacct tcattgcaca | 1320 |
| aacactgaca tccaaggta taagaagga gatttaactc tgtatgccat aaacctccat | 1380 |
| aacgtcacca gtacttgcg gttaccctat ccttttttcta caagcaagt ggataaatac | 1440 |
| cttctaagac ctttgggacc tcatggatta cttccaaat ctgtccaact caatggtcta | 1500 |
| actctaaaga tggtggatga tcaaaccttg ccacctttaa tggaaaaacc tctccggcca | 1560 |
| ggaagttcac tgggcttgcc agctttctca tatagttttt ttgtgataag aaatgccaaa | 1620 |
| gttgctgctt gcatctgaaa ataaaatata ctagtcctga cactgaaaa | 1669 |

<210> SEQ ID NO 18
<211> LENGTH: 545
<212> TYPE: PRT
<213> ORGANISM: Homo Sapiens

<400> SEQUENCE: 18

Met Leu Leu Arg Ser Lys Pro Ala Leu Pro Pro Pro Leu Leu Met Leu
1               5                   10                  15

Leu Leu Leu Gly Pro Leu Gly Pro Leu Ser Pro Gly Ala Leu Pro Arg
            20                  25                  30

```
Pro Ala Gln Ala Gln Gln Asp Val Val Asp Leu Asp Phe Phe Thr Gln
         35                  40                  45
Glu Pro Leu His Leu Val Ser Pro Ser Phe Leu Ser Val Thr Ile Asp
 50                  55                  60
Ala Asn Leu Ala Thr Asp Pro Arg Phe Leu Ile Leu Leu Gly Ser Pro
 65                  70                  75                  80
Lys Leu Arg Thr Leu Ala Arg Gly Leu Ser Pro Ala Tyr Leu Arg Phe
                 85                  90                  95
Gly Gly Thr Lys Thr Asp Phe Leu Ile Phe Asp Pro Lys Lys Glu Ser
                100                 105                 110
Thr Phe Glu Glu Arg Ser Tyr Trp Gln Ser Gln Val Asn Gln Asp Ile
        115                 120                 125
Cys Lys Tyr Gly Ser Ile Pro Pro Asp Val Glu Lys Leu Arg Leu
        130                 135                 140
Glu Trp Pro Tyr Gln Glu Gln Leu Leu Leu Arg Glu His Tyr Gln Lys
145                 150                 155                 160
Lys Phe Lys Asn Ser Thr Tyr Ser Arg Ser Val Asp Val Leu Tyr
                165                 170                 175
Thr Phe Ala Asn Cys Ser Gly Leu Asp Leu Ile Phe Gly Leu Asn Ala
                180                 185                 190
Leu Leu Arg Thr Ala Asp Leu Gln Trp Asn Ser Ser Asn Ala Gln Leu
        195                 200                 205
Leu Leu Asp Tyr Cys Ser Ser Lys Gly Tyr Asn Ile Ser Trp Glu Leu
210                 215                 220
Gly Asn Glu Pro Asn Ser Phe Leu Lys Lys Ala Asp Ile Phe Ile Asn
225                 230                 235                 240
Gly Ser Gln Leu Gly Glu Asp Phe Ile Gln Leu His Lys Leu Leu Arg
                245                 250                 255
Lys Ser Thr Phe Lys Asn Ala Lys Leu Tyr Gly Pro Asp Val Gly Gln
                260                 265                 270
Pro Arg Arg Lys Thr Ala Lys Met Leu Lys Ser Phe Leu Lys Ala Gly
        275                 280                 285
Gly Glu Val Ile Asp Ser Val Thr Trp His His Tyr Tyr Leu Asn Gly
        290                 295                 300
Arg Thr Ala Thr Arg Glu Asp Phe Leu Asn Pro Asp Val Leu Asp Ile
305                 310                 315                 320
Phe Ile Ser Ser Val Gln Lys Val Phe Gln Val Val Glu Ser Thr Arg
                325                 330                 335
Pro Gly Lys Lys Val Trp Leu Gly Glu Thr Ser Ser Ala Tyr Gly Gly
                340                 345                 350
Gly Ala Pro Leu Leu Ser Asp Thr Phe Ala Ala Gly Phe Met Trp Leu
        355                 360                 365
Asp Lys Leu Gly Leu Ser Ala Arg Met Gly Ile Glu Val Val Met Arg
        370                 375                 380
Gln Val Phe Phe Gly Ala Gly Asn Tyr His Leu Val Asp Glu Asn Phe
385                 390                 395                 400
Asp Pro Leu Pro Asp Tyr Trp Leu Ser Leu Leu Phe Lys Lys Leu Val
                405                 410                 415
Gly Thr Lys Val Leu Met Ala Ser Val Gln Gly Ser Lys Arg Arg Lys
                420                 425                 430
Leu Arg Val Tyr Leu His Cys Thr Asn Thr Asp Asn Pro Arg Tyr Lys
        435                 440                 445
```

-continued

```
Glu Gly Asp Leu Thr Leu Tyr Ala Ile Asn Leu His Asn Val Thr Lys
    450             455                 460

Tyr Leu Arg Leu Pro Tyr Pro Phe Ser Asn Lys Gln Val Asp Lys Tyr
465             470                 475                 480

Leu Leu Arg Pro Leu Gly Pro His Gly Leu Leu Ser Lys Ser Val Gln
            485                 490                 495

Leu Asn Gly Leu Thr Leu Lys Met Val Asp Asp Gln Thr Leu Pro Pro
            500                 505                 510

Leu Met Glu Lys Pro Leu Arg Pro Gly Ser Ser Leu Gly Leu Pro Ala
        515                 520                 525

Phe Ser Tyr Ser Phe Phe Val Ile Arg Asn Ala Lys Val Ala Ala Cys
        530                 535                 540

Ile
545
```